(12) United States Patent
Muraki et al.

(10) Patent No.: US 9,958,375 B2
(45) Date of Patent: May 1, 2018

(54) MICROPARTICLE SORTING APPARATUS AND DELAY TIME DETERMINATION METHOD

(71) Applicant: Sony Corporation, Tokyo (JP)

(72) Inventors: Yosuke Muraki, Tokyo (JP); Akiko Tsuji, Kanagawa (JP); Takashi Miyata, Tokyo (JP)

(73) Assignee: Sony Corporation, Tokyo (JP)

( * ) Notice: Subject to any disclaimer, the term of this patent is extended or adjusted under 35 U.S.C. 154(b) by 61 days.

(21) Appl. No.: 15/093,879

(22) Filed: Apr. 8, 2016

(65) Prior Publication Data

US 2016/0223451 A1    Aug. 4, 2016

Related U.S. Application Data

(62) Division of application No. 13/788,075, filed on Mar. 7, 2013, now Pat. No. 9,339,823.

(30) Foreign Application Priority Data

Mar. 30, 2012  (JP) ................................. 2012-080192

(51) Int. Cl.
*G01N 21/00* (2006.01)
*G01N 15/14* (2006.01)
(Continued)

(52) U.S. Cl.
CPC ......... *G01N 15/1425* (2013.01); *B03C 7/003* (2013.01); *G01N 15/1429* (2013.01);
(Continued)

(58) Field of Classification Search
CPC ........... G01N 15/1404; G01N 15/1434; G01N 15/1459; G01N 15/1484;
(Continued)

(56) References Cited

U.S. PATENT DOCUMENTS 6,079,836 A   6/2000  Burr et al.
6,248,590 B1  6/2001  Malachowski
(Continued)

FOREIGN PATENT DOCUMENTS

CN   1950690 A    4/2007
JP   56-033052 A  4/1981
(Continued)

*Primary Examiner* — Joseph C Rodriguez
(74) *Attorney, Agent, or Firm* — Wolf, Greenfield & Sacks, P.C.

(57) ABSTRACT

A microparticle sorting apparatus includes a detection unit which detects microparticles flowing through a flow path; an imaging device which images a droplet containing the microparticles which is discharged from an orifice provided on an edge portion of the flow path; a charge unit which applies a charge to the droplets; and a control unit which determines a delay time as from a time that the microparticles are detected by the detection unit to the time at which a number of bright spots in a standard region, which is set beforehand, of image information imaged by the imaging device reaches the maximum, making it possible for the charge unit to apply a charge to the microparticles once the delay time has lapsed after the microparticles are detected by the detection unit.

6 Claims, 12 Drawing Sheets

(51) Int. Cl.
*B03C 7/00* (2006.01)
*G01N 15/00* (2006.01)
*G01N 15/10* (2006.01)

(52) U.S. Cl.
CPC . *G01N 15/1434* (2013.01); *G01N 2015/0065* (2013.01); *G01N 2015/1006* (2013.01); *G01N 2015/1081* (2013.01); *G01N 2015/144* (2013.01); *G01N 2015/149* (2013.01); *G01N 2015/1481* (2013.01)

(58) Field of Classification Search
CPC ... G01N 2015/1409; G01N 2015/1422; G01N 2015/1481; B01L 3/502761; B01L 3/502766
See application file for complete search history.

(56) References Cited

U.S. PATENT DOCUMENTS

| | | | |
|---|---|---|---|
| 7,232,687 B2 * | 6/2007 | Lary | G01N 15/1404 209/127.4 |
| 7,417,734 B2 | 8/2008 | Kanda | |
| 8,795,500 B2 | 8/2014 | Shinoda | |
| 8,922,646 B2 | 12/2014 | Neckels et al. | |
| 8,975,595 B2 | 3/2015 | Norton et al. | |
| 9,029,724 B2 | 5/2015 | Hashimoto et al. | |
| 9,034,259 B2 * | 5/2015 | Kanda | G01N 15/14 422/50 |
| 9,087,371 B2 | 7/2015 | Muraki | |
| 9,134,220 B2 * | 9/2015 | Malachowski | G01N 15/1475 |
| 9,255,874 B2 * | 2/2016 | Sharpe | G01N 15/1404 |
| 9,339,823 B2 | 5/2016 | Muraki et al. | |
| 9,696,257 B2 * | 7/2017 | Fox | G01N 21/64 |
| 9,726,527 B2 * | 8/2017 | Norton | G01F 1/661 |
| 9,784,659 B2 | 10/2017 | Tanase et al. | |
| 9,784,660 B2 | 10/2017 | Otsuka et al. | |
| 2005/0227362 A1 | 10/2005 | Lary et al. | |
| 2008/0293146 A1 | 11/2008 | Frazier et al. | |
| 2011/0221892 A1 | 9/2011 | Neckels et al. | |
| 2013/0256136 A1 | 10/2013 | Muraki et al. | |
| 2013/0258075 A1 | 10/2013 | Muraki et al. | |
| 2014/0087453 A1 | 3/2014 | Tahara | |
| 2014/0144817 A1 | 5/2014 | Hashimoto et al. | |
| 2014/0193059 A1 | 7/2014 | Muraki | |
| 2014/0208875 A1 | 7/2014 | Muraki | |
| 2015/0050638 A1 | 2/2015 | Marquette | |
| 2015/0057787 A1 | 2/2015 | Muraki et al. | |
| 2015/0068957 A1 | 3/2015 | Otsuka et al. | |
| 2015/0204774 A1 | 7/2015 | Ito | |
| 2015/0285726 A1 | 10/2015 | Tanase et al. | |
| 2015/0285727 A1 | 10/2015 | Muraki | |
| 2015/0377763 A1 | 12/2015 | Brun et al. | |
| 2016/0245736 A1 | 8/2016 | Muraki et al. | |
| 2016/0266027 A1 | 9/2016 | Muraki et al. | |
| 2017/0010203 A1 * | 1/2017 | Otsuka | B01L 3/502776 |

FOREIGN PATENT DOCUMENTS

| | | |
|---|---|---|
| JP | 60-139350 A | 7/1985 |
| JP | 61-052714 A | 3/1986 |
| JP | 62-167478 A | 7/1987 |
| JP | 04-048245 A | 2/1992 |
| JP | 06-288896 A | 10/1994 |
| JP | 2007-532874 A | 11/2007 |
| JP | 2010-025911 A | 2/2010 |
| JP | 2010-190680 A | 9/2010 |
| WO | WO 2009/078307 A1 | 6/2009 |

* cited by examiner

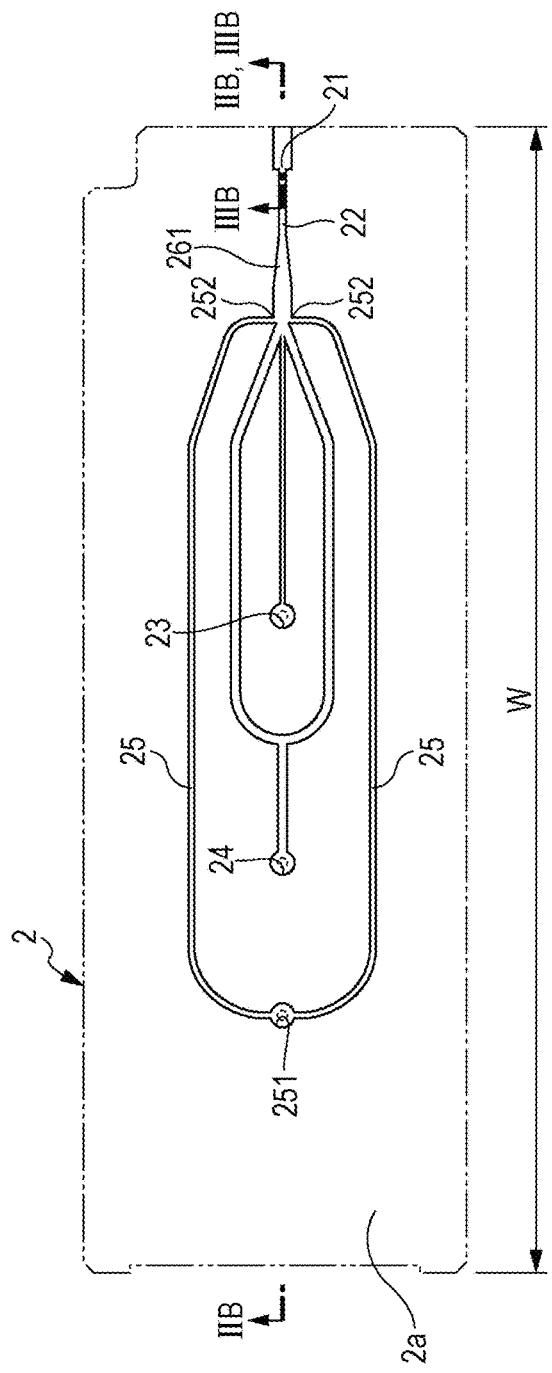
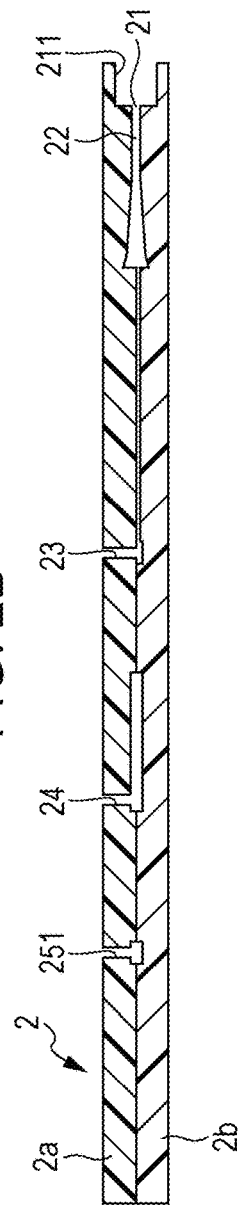

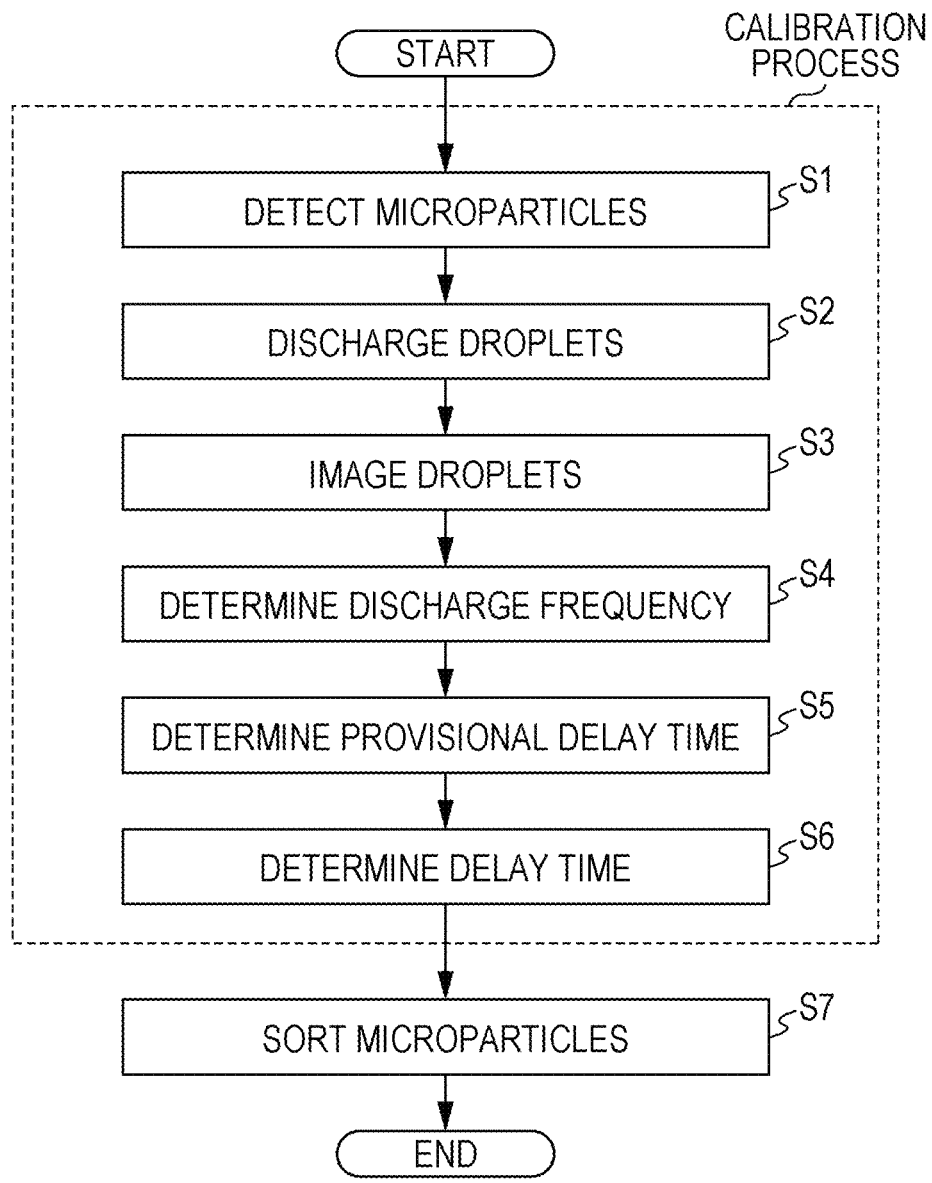

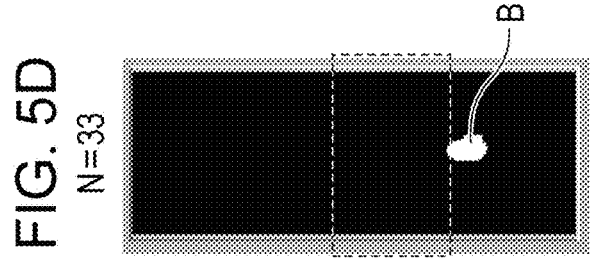
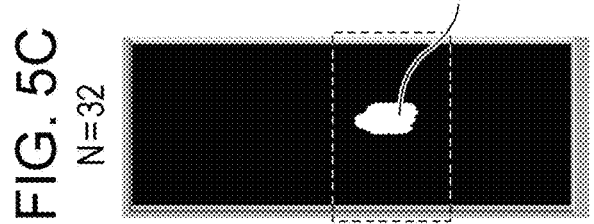
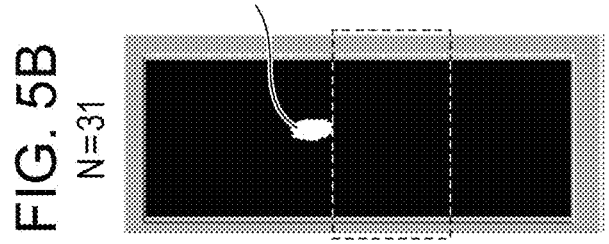
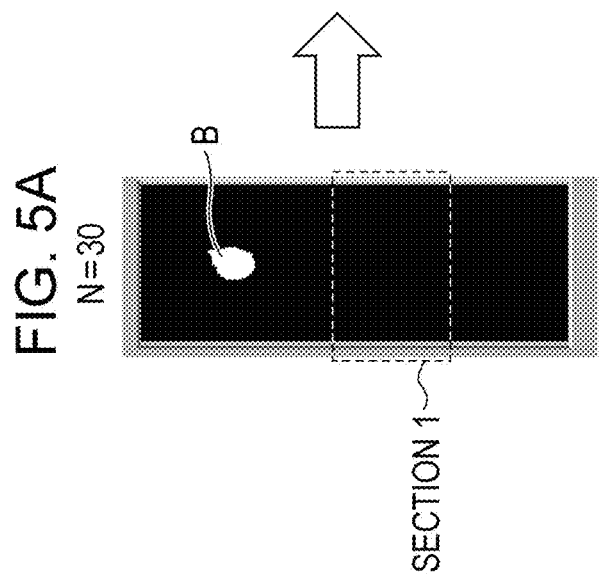

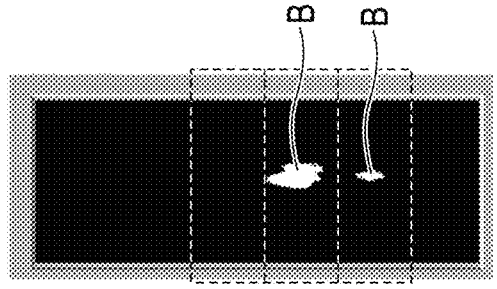
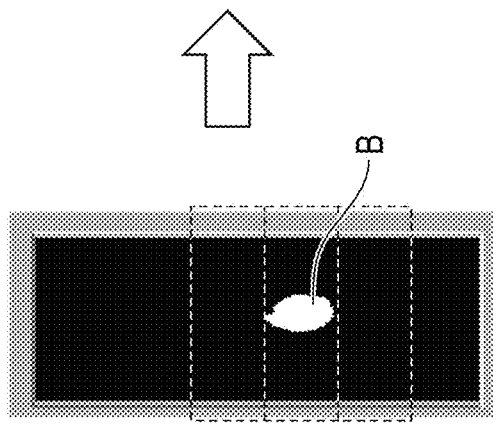
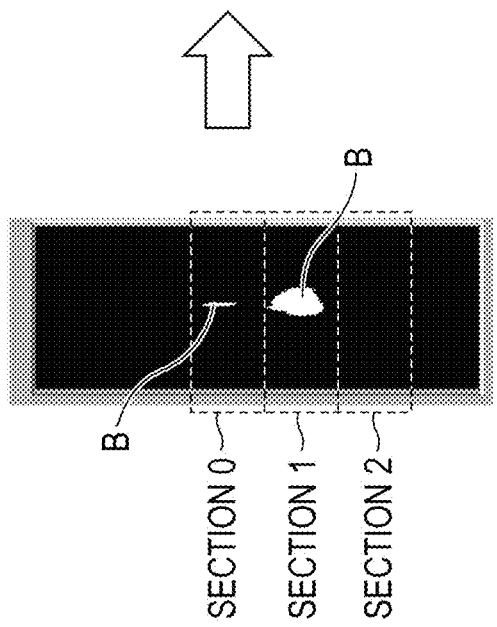

MICROPARTICLE SORTING APPARATUS AND DELAY TIME DETERMINATION METHOD

RELATED APPLICATIONS

This application is a divisional of and claims the benefit under 35 U.S.C. § 120 of U.S. patent application Ser. No. 13/788,075, titled "MICROPARTICLE SORTING APPARATUS AND DELAY TIME DETERMINATION METHOD," filed on Mar. 7, 2013, which claims the benefit under 35 U.S.C. § 119 of Japanese Patent Application JP 2012-080192, filed in the Japanese Patent Office on Mar. 30, 2012, each of which is hereby incorporated by reference in its entirety.

BACKGROUND

The present technology relates to a microparticle sorting apparatus and a delay time determination method in the microparticle sorting apparatus. More specifically, the present technology relates to a microparticle sorting apparatus or the like which automatically determines the delay time.

In the related art, there is a microparticle sorting apparatus (for example, a flow cytometer) which optically, electrically, or magnetically detects the characteristics of microparticles such as cells, then separates and collects only the microparticles which have predetermined characteristics.

In cell separation in a flow cytometer, first, a droplet stream (a laminar flow of a sample fluid containing cells and a sheath fluid) is generated from an orifice formed in the flow cell, the fluid stream is made into droplets by applying oscillation to the orifice, and a charge is applied to the droplets. Furthermore, the movement direction of the droplets containing the cells discharged from the orifice is electrically controlled and the target cells having the desired characteristics and the other non-target cells are collected in separate collection containers.

For example, Japanese Unexamined Patent Application Publication No. 2010-190680 discloses, as a microchip-type flow cytometer, "a microparticle sorting apparatus including: a microchip on which a flow path through which a fluid containing microparticles flows, and an orifice which discharges a fluid which flows through a flow path to a space outside of the chip are installed; an oscillating element for making a fluid into droplets in the orifice and discharging them; an electrical charging means for applying a charge to the discharged droplets; an optical detection means for detecting the optical characteristics of the microparticles flowing though the flow path; an electrode couple installed opposing one another to interpose the moving droplets; and two or more containers which collect the droplets which passed between the opposing electrodes".

In addition, Japanese Unexamined Patent Application Publication (Translation of PCT Application) No. 2007-532874 discloses a method in which control is performed on the operation of a flow cytometer which is capable of confirming whether or not the droplets have been sorted into an intended flow path by disposing auxiliary lighting and a detection unit in the position at which the droplets break off from the fluid (hereinafter, referred to as the break-off point). By ascertaining the break-off point in this manner, it is possible to ascertain the delay time from when the microparticles, which are cells or the like, are detected until the droplets containing the cells or the like reach the break-off point, and it is possible to apply a charge to the droplets containing the microparticles which are detected based on the delay time.

SUMMARY

However, the break-off point fluctuates according to the discharge conditions of the droplets and the like, and therefore the delay time also fluctuates. In addition, it is difficult to sufficiently ascertain an accurate timing to apply a charge to the droplets containing the microparticles by only ascertaining the break-off point. Therefore, the correct charge is applied to the droplets which contain the microparticles, but in the end, methods have mostly been adopted in which the user visually discriminates whether the droplets have been allotted to the desired collection container or not by observing the droplets, to which a charge is applied, on a preparation. Such methods demanded that the user have a mastery of the technology, and there are problems with the reliability and stability.

Therefore, it is desirable to provide a microparticle sorting apparatus which is capable of automatically, simply, and accurately applying a charge to droplets.

According to an embodiment of the present technology, there is provided a microparticle sorting device including a detection unit which detects microparticles flowing through a flow path; an imaging device which images droplets containing the microparticles which are discharged from an orifice provided on an edge portion of the flow path; a charge unit which applies a charge to the droplets; and a control unit which determines a delay time as from a time that the microparticles are detected by the detection unit to the time at which the number of bright spots in a standard region, which is set beforehand, of image information imaged by the imaging device reaches the maximum, making it possible for the charge unit to apply a charge to the microparticles once the delay time has lapsed after the microparticles are detected by the detection unit.

According to the microparticle sorting apparatus, it is possible to automatically determine the delay time based on the number of bright spots within the standard region without asking for the user to perform setting.

In the microparticle sorting apparatus, the imaging device may image images of a plurality of the droplets at a plurality of different times, and the control unit may preliminarily determine the delay time using the time from when the microparticles are detected by the detection unit to the time at which the number of bright spots within the standard region, which is calculated by comparing the image information of the plurality of droplets imaged by the imaging device, reaches a maximum as a provisional delay time.

In the microparticle sorting apparatus, the imaging device may image the images of the plurality of droplets within a shorter time than a discharge interval time of each of the droplets once the provisional delay time has elapsed from the time at which the microparticles are detected by the detection unit, and the control unit may update the provisional delay time and determine the delay time by referring to adjacent information relating to the number of the bright spots in at least one of two comparison regions that are adjacent to the standard region in relation to a discharge direction of the droplets in the image information.

In the microparticle sorting apparatus, of the two comparison regions, a first comparison region and a second comparison region may be arranged in order in a discharge direction of the droplets, and the control unit may calculate the time at which the number of bright spots reaches a predetermined percentage of the maximum value in the second comparison region in a process where the number of bright spots increases toward the time at which the number of bright spots reaches the maximum in the second comparison region, and may determine the time to be the time at which the number of bright spots within the standard region reaches a maximum.

In the microparticle sorting apparatus, of the two comparison regions, a first comparison region and a second comparison region may be arranged in order in a discharge direction of the droplets, and the control unit may calculate the first time at which the number of bright spots reaches a predetermined percentage of the maximum value in the first comparison region in a process where the number of bright spots decreases from the time at which the number of bright spots reaches the maximum in the first comparison region, may calculate the second time at which the number of bright spots reaches a predetermined percentage of the maximum value in the second comparison region in a process where the number of bright spots increases toward the time at which the number of bright spots reaches the maximum in the second comparison region, and may determine the time in which the number of bright spots within the standard region reaches a maximum as (the first time+the second time)/2.

In the microparticle sorting apparatus, the control unit may adjust a discharge frequency of the droplets, and determines the optimal discharge frequency of the droplets to be the discharge frequency at which the break-off point, where the droplets start forming in the discharge direction of the droplets, is closest to the orifice.

In addition, the microparticle sorting apparatus may further include a pair of deflection plates disposed opposite one another to interpose the droplets imaged by the imaging device, which change a progression direction of the droplets using an electrical force which acts between the deflection plates and the charge.

In addition, the microparticle sorting apparatus may also be a microchip-type flow cytometer in which the orifice and the flow path are provided in the microchip.

Furthermore, the term "delay time" here refers to the delay time from the time at which the microparticles are detected by the detection unit to when the droplets are formed from the fluid containing the microparticles. In other words, "delay time" refers to the necessary time from the time that the microparticles are detected by the detection unit to when the droplets containing the microparticles have a charge applied thereto. In the present technology, this refers to the duration of from the time at which the microparticles are detected by the detection unit, to the time at which the number of bright spots within the standard region, which is set beforehand, in the image information imaged by the imaging device reaches the maximum.

In addition, the term "provisional delay time" refers to a provisional delay time until the delay time is determined. More specifically, "provisional delay time" refers to the time from when the microparticles are detected by the detection unit to the time at which the number of bright spots in the standard region, which is calculated by comparing the plurality of items of image information of the droplets imaged by the imaging device, reaches the maximum. In addition, an example of the imaging device includes a droplet camera or the like.

In addition, according to another embodiment of the present technology, there is provided a delay time determination method including a process of causing a microparticle sorting device to detect microparticles flowing through the flow path, causing a microparticle sorting device to image the droplets containing the microparticles discharged from the orifice provided on the edge portion of the flow path, and causing a microparticle sorting device to determine the delay time as from the time that the microparticles are detected until the time at which the number of bright spots within the standard region, which is set beforehand, in the image information of the imaged droplets reaches the maximum.

In addition, in the method, a process may also be included which images the images of each of a plurality of droplets at a plurality of times, performs preliminarily determination of the delay time using the period from when the microparticles are detected until the time at which the number of bright spots in the standard region, which is calculated by comparing the image information of each of the plurality of droplets which are imaged, reaches the maximum as the provisional delay time.

In addition, in the method, a process may also be included which images the images of the plurality of droplets within a shorter time than a discharge interval time of each of the droplets once the provisional delay time has elapsed from the time at which the microparticles are detected, and updates the provisional delay time and determines the delay time by referring to adjacent information relating to the number of the bright spots in at least one of two comparison regions that are adjacent to the standard region in relation to a discharge direction of the droplets in the image information.

In addition, in the method, a process may also be included in which, of the two comparison regions, a first comparison region and a second comparison region are arranged in order in a discharge direction of the droplets, the first time at which the number of bright spots reaches a predetermined percentage of the maximum value in the second comparison region in a process where the number of bright spots increases toward the time at which the number of bright spots reaches the maximum in the second comparison region is calculated, and the second time to be the time at which the number of bright spots within the standard region reaches the maximum is determined.

In addition, in the method, a process may also be included in which, of the two comparison regions, a first comparison region and a second comparison region are arranged in order in a discharge direction of the droplets, the time at which the number of bright spots reaches a predetermined percentage of the maximum value in the first comparison region in a process where the number of bright spots decreases from the time at which the number of bright spots reaches the maximum in the first comparison region is calculated, the time at which the number of bright spots reaches a predetermined percentage of the maximum value in the second comparison region in a process where the number of bright spots increases toward the time at which the number of bright spots reaches the maximum in the second comparison region is calculated, and the time in which the number of bright spots within the standard region reaches a maximum is determined as (the first time+the second time)/2.

In the present technology, the term "microparticle" widely includes organism related microparticles such as cells, microorganisms and liposomes, or synthetic particles such as latex particles, gel particles and particles for industrial use.

The organism related microparticles include chromosomes, liposomes, mitochondria, organelles and the like which various types of cell contain. The cells include animal cells (hematopoietic cells and the like) and plant cells. Microorganisms include bacteria such as *Escherichia coli*, viruses such as the tobacco mosaic virus, and fungi such as yeast. Furthermore, for the organism related microparticles, nucleic acid and protein, and organism related polymers such as complexes thereof may also be included. In addition, particles for industrial use may also be, for example, organic or inorganic polymeric materials, metals, and the like. The organic polymeric materials include polystyrene, divinylbenzene styrene, polymethyl methacrylate, and the like. The inorganic polymer materials include glass, silica, magnetic materials, and the like. The metals include metal colloid, aluminum, and the like. It is normal for the shape of these microparticles to be generally spherical, however, they may also be non-spherical, and the size, mass, and the like thereof is not particularly limited.

It is desirable to provide a microparticle sorting apparatus which is capable of automatically, simply, and accurately applying a charge to droplets.

BRIEF DESCRIPTION OF THE DRAWINGS

FIGS. 2A and 2B are schematic views for illustrating an example of a microchip which may be installed in the flow cytometer;

FIG. 4 is a flow diagram for illustrating the method of determining the delay time in the flow cytometer;

FIGS. 5A to 5D are explanatory diagrams, which are photographs showing examples of images of a droplet imaged by a droplet camera of the flow cytometer, for illustrating the provisional delay time determination step;

FIGS. 7A to 7C are explanatory diagrams, which are photograph showing examples of images of the droplets imaged by the droplet camera of the flow cytometer, for illustrating the delay time determination step;

DETAILED DESCRIPTION OF EMBODIMENTS

Hereafter, description will be given of favorable embodiments for realizing the present technology with reference to the drawings. Furthermore, the embodiments described below represent an example of a representative embodiment of the present technology, and the scope of the present technology is not to be interpreted narrowly according to this example. The description will be given in the following order.

Figure 1:
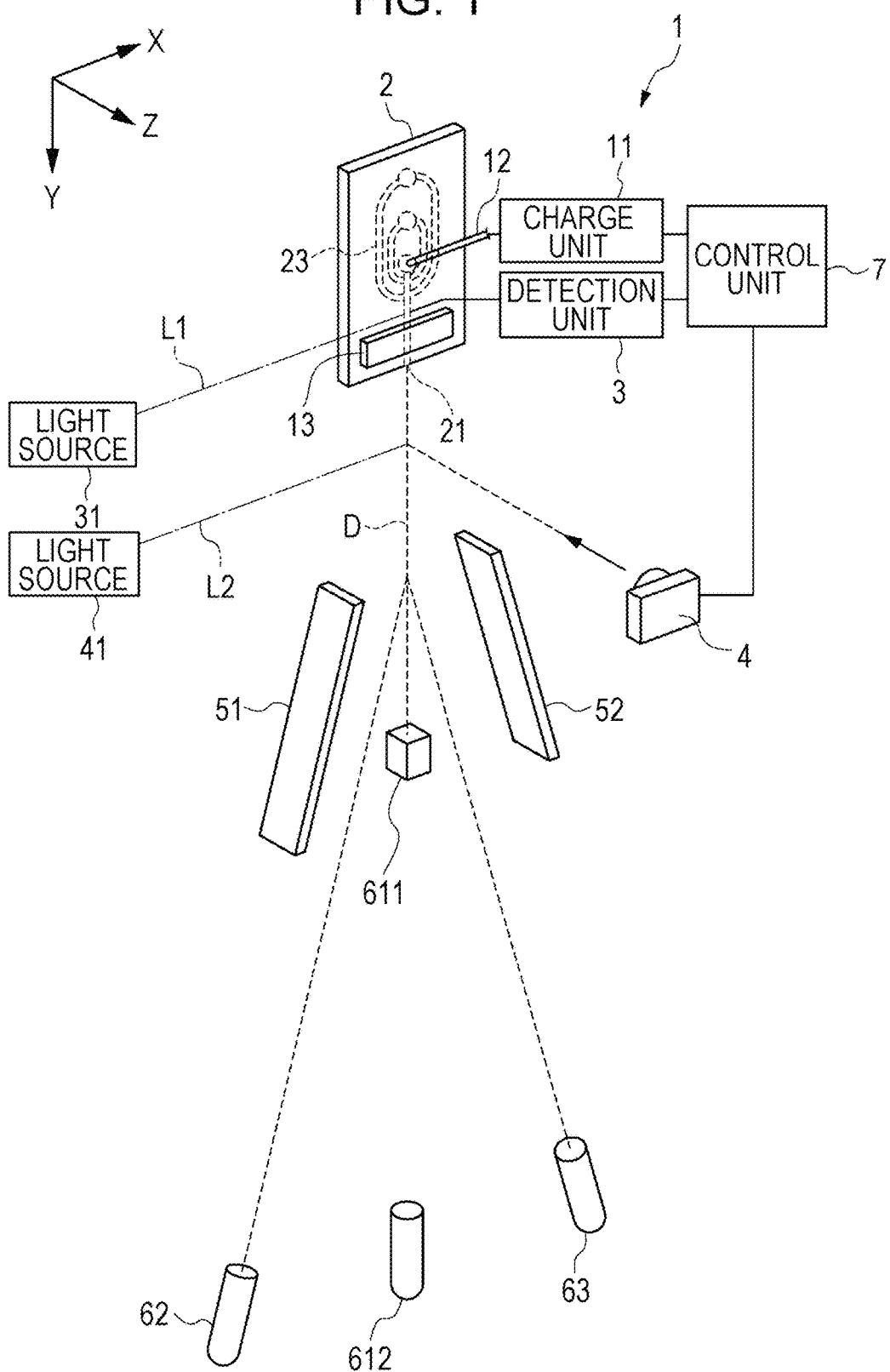
FIG. 1 is a schematic view for illustrating the configuration of the sorting system of a microparticle sorting apparatus (a flow cytometer) according to an embodiment of the present technology which is configured as a microchip-type flow cytometer.

1. Apparatus Configuration of Microparticle Sorting Apparatus according to Present Technology
1-1 Charge Unit
1-2 Microchip
1-3 Detection Unit
1-4 Droplet Camera
1-5 Deflection Plate
1-6 Collection Container
1-7 Control Unit or Similar
2. Delay Time Determination Method in Microparticle Sorting Apparatus according to Present Technology
2-1 Microparticle Detection Step $S_1$
2-2 Droplet Discharge Step $S_2$
2-3 Droplet Imaging Step $S_3$
2-4 Discharge Frequency Determination Step $S_4$
2-5 Provisional Delay Time Determination Step $S_5$
2-6 Delay Time Determination Step $S_6$
2-6-1 First Delay Time Determination Method
2-6-2 Second Delay Time Determination Method
2-7 Microparticle Sorting Step $S_7$
2-7-1 Microparticle Detection Step $S_{71}$
2-7-2 Droplet Discharge and Charge Application Step $S_{72}$ 1. Apparatus Configuration of Microparticle Sorting Apparatus according to Present Technology FIG. 1 is a schematic view for illustrating the configuration of the sorting system of the microparticle sorting apparatus 1 (hereinafter also referred to as "the flow cytometer 1") according to an embodiment of the present technology which is configured as a microchip-type flow cytometer.

1-1 Charge Unit

The flow cytometer 1 is provided with a charge unit 11 which applies a charge to the droplets discharged from the orifice 21 formed on the microchip 2. The charging of the droplets is performed by electrodes 12, which are electrically connected to the charge unit 11 and inserted into a sample inlet 23 provided on the microchip 2. Furthermore, it is sufficient for the electrodes 12 to be inserted to a location on the microchip 2 so as to make electrical contact with the sample fluid or the sheath fluid which is pumped down the flow path.

In the flow cytometer 1, it is possible for the charge unit 11 to charge the droplets containing the microparticles once the delay time has elapsed after the microparticles contained in the sample fluid are detected by a detection unit 3 described below. Here, the term "delay time" refers to the delay time from the time that the microparticles are detected by the detection unit 3 to when droplets are formed from the fluid containing the microparticles. In other words, "delay time" refers to the necessary time from the time that the microparticles are detected by the detection unit 3 to when the droplets containing the microparticles have a charge applied thereto by the charge unit 11. In the present technology, the term "delay time" refers to the duration of from the time at which the microparticles are detected by the detection unit 3, to the time at which the number of bright spots within the standard region, which is set beforehand, in the image information imaged by the droplet camera 4 described below reaches a maximum.

1-2 Microchip

FIGS. 2A and 2B and FIGS. 3A to 3C show an example of the microchip 2 which may be installed in the flow cytometer 1.

Figure 3A:
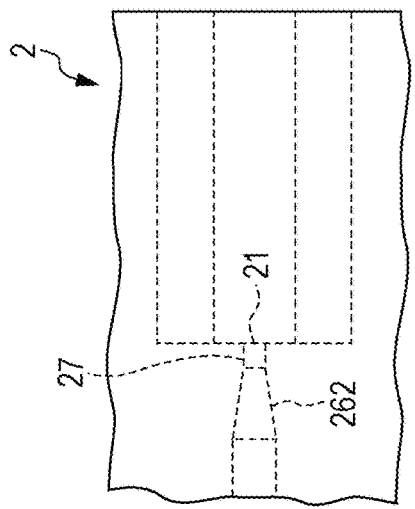
FIGS. 3A to 3C are schematic views for illustrating the configuration of an orifice of the microchip.
Figure 3B:
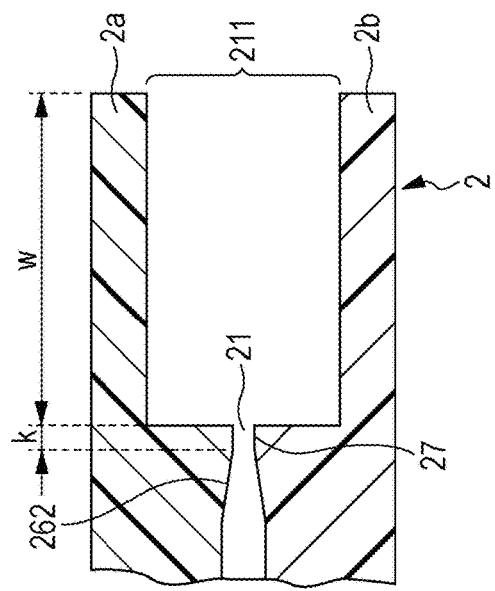
Figure 3C:
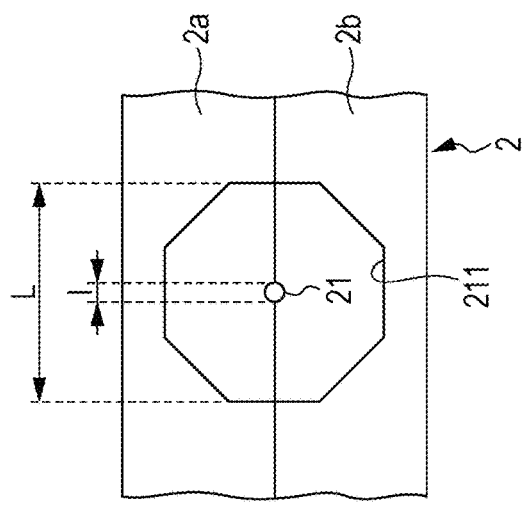

FIG. 2A shows a schematic view of the upper surface, and FIG. 2B shows a cross-sectional schematic view corresponding to the line IIB-IIB in FIG. 2A. In addition, FIGS. 3A to 3C schematically illustrate the configuration of the orifice 21 of the microchip 2, FIG. 3A shows an upper surface schematic view, FIG. 3B shows a cross-section schematic view, and FIG. 3C shows a front surface schematic view. FIG. 3B corresponds to the cross section along the line IIIB-IIIB in FIG. 2A.

The microchip 2 is formed of substrate layers 2a and 2b which are bonded together to form a sample flow path 22. It is possible to perform the formation of the sample flow path 22 from the substrate layers 2a and 2b through injection molding of a thermoplastic resin using a metal mold. For the thermoplastic resin, plastics generally used in the related art as microchip materials such as polycarbonate, polymethyl methacrylate resin (PMMA), cyclic polyolefin, polyethylene, polystyrene, polypropylene and polymethyl disilazane (PDMS) may be adopted.

The sample fluid is introduced to the sample inlet 23 from the fluid delivery connector portion, merges with the sheath fluid which is introduced from the fluid delivery connector portion to a sheath inlet 24, and is delivered through the sample flow path 22. The sheath fluid introduced from the sheath inlet 24, after being split into two directions and delivered, in the merging portion in which the sheath fluid merges with the sample fluid introduced from the sample inlet 23, the sheath fluid merges with the sample fluid so as to interpose the sample fluid from two directions. Therefore, in the merging portion, in the center of the sheath fluid laminar flow, a three-dimensional laminar flow in which the sample laminar flow is positioned is formed.

Reference numeral 25 represents a suction flow path for applying a negative pressure to the sample flow path 22 when clogging or bubbles occur in the sample flow path 22, which temporarily causes the flow to flow backward in order to resolve the clogging or bubbles. On one end of a suction flow path 25, a suction outlet 251 connected to a negative pressure source such as a vacuum pump via the liquid delivery connector portion is formed, and the other end is connected to the sample flow path 22 in a communication hole 252.

In the three-dimensional laminar flow, the laminar flow width is limited in a limiter portion 261 (refer to FIGS. 2A and 2B) and 262 (refer to FIGS. 3A to 3C) formed such that the surface area of the vertical cross section thereof in relation to the fluid delivery direction gets smaller gradually or in stages from upstream in the fluid delivery direction to downstream. After this, the three-dimensional laminar flow becomes a fluid stream (refer to FIG. 1) from the orifice 21 provided on one side of the flow path, and is discharged. In FIG. 1, the discharge direction of the fluid stream from the orifice 21 is represented by the Y axis positive direction.

The connection portion to the orifice 21 of the sample flow path 22 is a straight portion 27, which is formed linearly. The straight portion 27 functions such that the fluid stream from the orifice 21 is ejected in a straight line in the Y axis positive direction.

The fluid stream ejected from the orifice 21 is transformed into droplets by the oscillation applied to the orifice 21 by a chip excitation unit. The orifice 21 is open in the end face direction of the substrate layers 2a and 2b, and a notch portion 211 is provided between the opening position thereof and the substrate layer end face. The notch portion 211 is formed by notching the substrate layers 2a and 2b between the opening portion of the orifice 21 and the substrate end face such that the diameter L of the notch portion 211 is larger than the opening diameter l of the orifice 21 (refer to FIG. 3C). It is desirable to form the diameter L of the notch portion 211 two times or larger than the opening diameter l of the orifice 21 so as not to obstruct the movement of the droplets discharged from the orifice 21.

1-3 Detection Unit

The reference numeral 3 in FIG. 1 represents the detection unit which detects the measurement target light emitted from the microparticles such as cells through the irradiation of a laser L1 emitted from a light source 31. The detection unit 3 performs characteristic detection of the cells between the limiter portion 261 (refer to FIGS. 2A and 2B) and the limiter portion 262 (refer to FIGS. 3A to 3C) of the sample flow path 22. The characteristic detection is not particularly limited, however, for example, in a case in which optical detection is used, the scattered light and the fluorescent light emitted from the cells due to the irradiation of laser L1 (refer to FIG. 1) in relation to the cells which are fluid delivered arranged in a single row in the sample flow path 22 in the center of the three-dimensional laminar flow, are detected by the detection unit 3.

For the irradiation and detection of the light, in addition to the laser light source, irradiation systems that condense and irradiate a laser onto the cells such as a condensing lens, a dichroic mirror or a band pass filter may also be configured. The detection system is, for example, configured by an area imaging device such as a PMT (photo multiplier tube), or a CCD or CMOS device.

The measurement target light detected by the detection system of the detection unit 3 is light emitted from the cells due to the irradiation of the measurement light, and for example, may be scattered light, fluorescent light or the like such as forward scattered light, side scattered light, Rayleigh scattering, or Mie scattering. These measurement target lights are converted into an electrical signal, output to a control unit 7, and utilized in the optical characteristic discrimination of the cells.

Furthermore, the detection unit 3 may also detect the characteristics of the cells magnetically or electrically. In this case, microelectrodes are disposed opposing one another in the sample flow path 22 of the microchip 2, and the resistance value, the capacitance value, the inductance value, the impedance, the change value of the electric field between the electrodes, or the magnetization, the change in the magnetic field, or the like are measured.

1-4 Droplet Camera

The reference numeral 4 in FIG. 1 represents an example of the imaging device of the present technology, which is a droplet camera for imaging the droplet D discharged from the orifice 21 of the microchip 2 such as a CCD camera, a CMOS sensor, or the like. The droplet camera 4 is designed such that it is possible to perform focus adjustment of the image of the droplet D which is imaged. In the flow cytometer 1, the droplets containing microparticles such as cells are irradiated by a laser L2 emitted from the light source 41, and the microparticles are excited while the droplet D is imaged by the droplet camera 4, thereby the flow cytometer 1 is designed such that the user can confirm that the microparticles are contained in the droplets from the display unit.

In addition, in the flow cytometer 1, due to the microchip being exchanged for a new microchip, or the external environment (the temperature and the like) changing, there are cases in which it is necessary to change the droplet formation parameters (sheath pressure, droplet frequency, piezo drive pressure, and the like). In this case, it is necessary to adjust the time until the charge is applied to the droplets containing the microparticles after the microparticles are detected by the detection unit 3 (hereinafter, this time is also referred to as the delay time). The droplet camera 4 functions in order to image the droplet D, and also in order to make it possible for the control unit 7 described below to determine the delay time.

More specifically, the droplet camera 4 is designed such that it is possible to image a plurality of images of the droplet D at a plurality of different times such that the control unit 7 described below may preliminarily determine the provisional delay time as the delay time. Furthermore, the term "provisional delay time" refers to the duration of from the time at which the microparticles are detected by the detection unit 3, to the time at which the number of bright spots within the standard region, which is calculated by comparing a plurality of items of image information of the droplets imaged by the droplet camera 4, reaches a maximum. In addition, the term "plurality of different times", for example, refers to each time, the interval between which is the time of the reciprocal of the frequency of the oscillation which an oscillating element 13 applies to the orifice 21 (in other words, the discharge interval time of each of the droplets D).

In addition, in order for the control unit 7 to be able to update the provisional delay time and determine the delay time, the droplet camera 4 is designed to be able to image a plurality of images of the droplet D within a predetermined time after the provisional delay time has elapsed from the time at which the microparticles are detected by the detection unit 3. Furthermore, the term "predetermined time" refers to a time shorter than the discharge interval time of each of the droplets D.

In addition, the droplet camera 4 is designed to be movable in the positive direction or the negative direction along the Y axis such that the control unit 7 may determine the optimal discharge frequency of the droplets D described below.

In addition, the images imaged by the droplet camera 4 are displayed on the display unit such as a display, and are also used to allow the user to confirm the formation state of the droplet D (the size, shape, interval, and the like of the droplet) in the orifice 21.

1-5 Deflection Plate

The reference numerals 51 and 52 in FIG. 1 represent a pair of deflection plates which are disposed opposite one another to interpose the droplet D which is ejected from the orifice 21 and imaged by the droplet camera 4. Deflection plates 51 and 52 are configured to contain the electrodes which control the movement direction of the droplets discharged from the orifice 21 using the electrical force on the charge applied to the droplets. In addition, the deflection plates 51 and 52 also control the trajectory of the droplet D emitted from the orifice 21 using the electrical force on the charge applied to the droplet D. In FIG. 1, the opposing direction of the deflection plates 51 and 52 is represented by the X axis direction.

1-6 Collection Container

In the flow cytometer 1, the droplet D is accepted by one of the plurality of collection containers 611, 612, 62, or 63 which are disposed in a row in the opposing direction of the deflection plates 51 and 52 (the X axis direction). The collection containers 611, 612, 62, or 63 may also be plastic tubes or glass tubes which are normally used for experiments. The number of the collection containers 611, 612, 62, or 63 is not particularly limited, however, here, a case in which four are disposed is illustrated. The droplet D emitted from the orifice 21 is guided into and collected in one of the four collection containers 611, 612, 62, or 63 according to the presence or absence, or alternatively the magnitude of the electrical force between the deflection plates 51 and 52.

The collection containers 611, 612, 62, and 63 are disposed in a container for use as the collection container (not shown) in an exchangeable manner. The container for use as the collection container (not shown) is disposed on the Z axis stage (not shown) configured to be movable in the direction (the Z axis direction) orthogonal to the discharge direction (the Y axis direction) of the droplet D from the orifice 21 and to the opposing direction (X axis direction) of the deflection plates 51 and 52.

1-7 Control Unit or Similar

The flow cytometer 1, in addition to the configuration described above, is provided with a data analysis unit for characteristic discrimination of the cells or the like detected by the detection unit 3, a tank portion for retaining the sample fluid and the sheath fluid, the control unit 7 for controlling each of the configurations described above, and the like which an ordinary flow cytometer is provided with.

The control unit 7 may be configured by an ordinary computer provided with a CPU, memory, a hard disk and the like, and on the hard disk is stored the OS, a program to execute each step relating to the delay time determination method described next, and the like.

2. Delay Time Determination Method in Microparticle Sorting Apparatus according to Present Technology 2-1 Microparticle Detection Step $S_1$ FIG. 4 is flow chart for illustrating the delay time determination step in the flow cytometer 1. The delay time determination step includes the processes of "microparticle detection step $S_1$", "droplet discharge step $S_2$", "droplet imaging step $S_3$", "discharge frequency determination step $S_4$", "provisional delay time determination step $S_5$", and "delay time determination step $S_6$". In addition, a process of "microparticle sorting step $S_7$" may also be executed after the delay time determination steps described above. Description will be given of each process below.

First, in the microparticle detection step $S_1$, the control unit 7 outputs a signal to the fluid delivery connector portion and begins fluid delivery of the sample fluid and the sheath fluid. Furthermore, the detection unit 3 detects the microparticles contained in the sample at the sample flow path 22 by, for example, the irradiation of the laser L. Furthermore, the present step $S_1$ and the steps $S_2$ to $S_6$ described below are a calibration process for determining the delay time from when the detection unit 3 detects the target cells or the like until the charge unit 11 applies a charge to the droplets containing the cells or the like. Therefore, it is preferable to use calibration beads such as particles for industrial use, the shape and the like of which is clear, beforehand as the microparticles.

2-2 Droplet Discharge Step $S_2$

In the droplet discharge step $S_2$, the oscillating element 13 applies an oscillation to the orifice 21, the droplet D is discharged from the orifice 21, the droplets D is collected in the waste fluid inlet, and it is possible to dispose of the fluid (refer to FIG. 4).

2-3 Droplet Imaging Step $S_3$

In the droplet imaging step $S_3$, the control unit 7 outputs a signal to the droplet camera 4, and the droplet camera 4 that received the signal images the droplet D which is discharged and excited by the laser L1 (refer to FIG. 4). The droplet camera 4 may image the images at an interval that is the same as or shorter than the interval of the droplet clock described below.

At this time, for example, the control unit 7 may output a signal to the droplet camera 4 and make the droplet camera 4 that received the signal move in the X axis direction or the Y axis direction. Furthermore, the control unit may perform focus adjustment in the Z axis direction in the imaging of the images of the droplet D by the droplet camera 4. For example, the control unit 7 may perform focus adjustment until the contrast ratio in the image imaged by the droplet camera 4 falls within a predetermined range.

2-4 Discharge Frequency Determination Step $S_4$

In the discharge frequency determination step $S_4$, the control unit 7 moves the droplet camera 4 to a predetermined position and adjusts the discharge frequency of the droplets D based on the image information imaged by the droplet camera 4 (refer to FIG. 4). The predetermined position described above is not particularly limited, however, it may be a position set beforehand according to the discharge conditions such as the orifice diameter and the drive pressure.

Furthermore, the control unit 7 determines the optimal discharge frequency of the droplets D to be the discharge frequency at which the position where the droplets D start forming in the Y axis direction (hereinafter referred to as the break-off point) is closest to the orifice 21. Furthermore, the present step $S_4$ may also be executed after the step $S_5$ described below.

In this manner, in the flow cytometer 1, since the optimal discharge frequency is determined by the control unit 7 based on the break-off point, it is possible to resolve the complication of the user setting the droplet frequency manually.

2-5 Provisional Delay Time Determination Step $S_5$

In the provisional delay time determination step $S_5$, the control unit 7 determines the provisional delay time of the droplet D by comparing the plurality of items of image information of the droplet D imaged by the droplet camera 4 from the time at which the microparticles are detected by the detection unit 3 (refer to FIG. 4).

The term "provisional delay time" here refers to the time which is provisionally treated as the delay time by the present step $S_5$, which is the period until the delay time is determined by the delay time step $S_6$ described below. More specifically, the term "provisional delay time" refers to the duration of from the time at which the microparticles are detected by the detection unit 3, to the time at which the number of bright spots within the standard region described below, which is calculated by comparing a plurality of items of image information of the droplet D imaged by the droplet camera 4 at a plurality of different times, reaches a maximum. Furthermore, the term "plurality of different times" is not particularly limited, however, for example, refers to each time, the interval between which is the time of the reciprocal of the frequency of the oscillation which the oscillating element 13 applies to the orifice 21 (in other words, refers to the discharge interval time of each of the droplets D, and is referred to as the "droplet clock" hereinafter).

FIGS. 5A to 5D are photographs showing examples of images of a droplet imaged by the droplet camera 4 of the flow cytometer 1, and represent the images which are imaged at different times (refer to FIGS. 5A to 5D). More specifically, FIGS. 5A to 5D are photographic views for illustrating which of the droplets the detected microparticles are contained in when the droplet D imaged by the droplet camera 4 at the time (T0) at which the microparticle is detected by the detection unit 3 is set as the first droplet. Furthermore, each photographic view may also be a view in which a plurality of imaged images are integrated together.

In FIGS. 5A to 5D, the term "Section 1" refers to the standard region set beforehand in the image P.

The control unit 7 compares the plurality of images of the droplet D imaged by the droplet camera 4 at the interval of the droplet clock, and preliminarily determines the time from T0 until when the number of the bright spots B within "Section 1" reaches a maximum as the provisional delay time. Furthermore, the term "bright spot" refers to pixels which have a higher brightness than a predetermined threshold in the image of the droplet D imaged by the droplet camera 4, and is an item of image information of the microparticles contained in the excited droplet D, irradiated by the laser L2.

In FIGS. 5A to 5D, as an example of the present technology, the term "bright spot" refers to the images which are imaged by the droplet camera 4 when the 30th to 33rd droplets are discharged, when the droplet D discharged from the orifice 21 at T0 and imaged by the droplet camera 4 is set as the first droplet. For example, the 30th droplet is the photographic view represented by N=30 (refer to FIG. 5A).

In the example shown in FIGS. 5A to 5D, the control unit 7 can discriminate that the microparticles are contained in the 32nd droplet based on the image information of N=32 (refer to FIG. 5C) in which the number of bright spots B within "Section 1" reaches a maximum. In other words, the control unit 7 compares the plurality of images of the droplet D imaged by the droplet camera 4 at the interval of the droplet clock, and can preliminarily determine the delay time from the time that the microparticles are detected until the time that the 32nd droplet is discharged as the provisional delay time.

In this manner, in the flow cytometer 1, it is possible to preliminarily determine the provisional delay time as the delay time by comparing the number of bright spots in the image information within "Section 1" in relation to a plurality of different times. Therefore, it is possible to simply, and accurately apply a charge to the droplets without demanding complicated operations of the user.

2-6 Delay Time Determination Step $S_6$

In the delay time determination step $S_6$ shown in FIG. 4, first, the control unit 7 refers to the adjacent information described below based on the plurality of images of the droplet D imaged by the droplet camera 4 within a shorter time than the droplet clock after the provisional delay time has elapsed from T0. Furthermore, the control unit 7 updates the provisional delay time which is preliminarily determined by the provisional delay time determination step $S_5$ described above, and may determine the delay time more precisely by referring to the adjacent information. The method is described below with reference to FIG. 6A to FIG. 11. Furthermore, the adjacent information is information related to the number of bright spots in the two comparison regions of standard regions which are adjacent in relation to the discharge direction of the droplets.

Figure 6A:
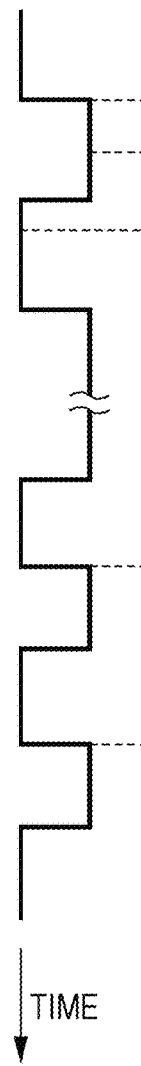
FIGS. 6A to 6C are explanatory diagrams for illustrating the delay time determination step in the flow cytometer.
Figure 6B:
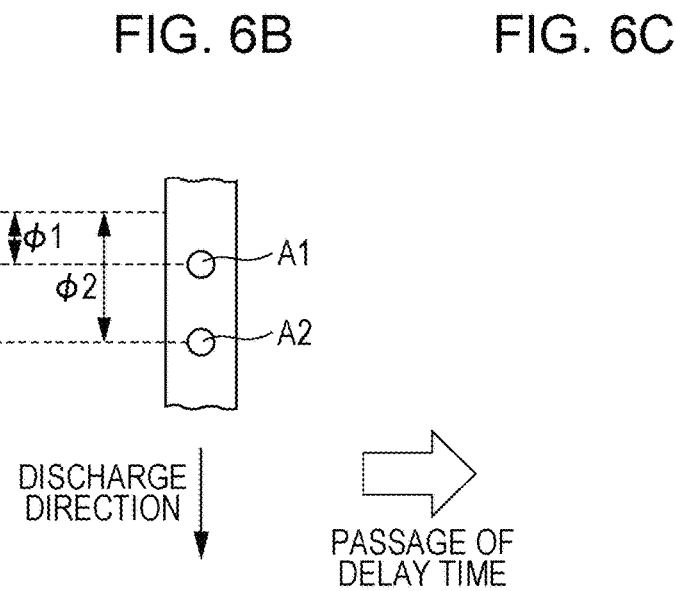
Figure 6C:
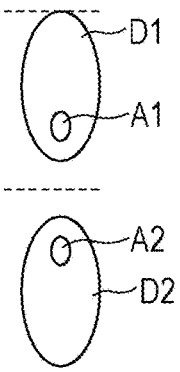

FIGS. 6A to 6C schematically show the transition from when the microparticles are detected by the detection unit 3 to the droplet D containing microparticles is imaged by the droplet camera 4.

FIG. 6A shows a graph of the droplet clock (Droplet CLK). Here, FIG. 6B shows the microparticles A1 and A2 which flow through the flow path of the microchip 2 and are detected by the detection unit 3. Furthermore, FIG. 6C shows the droplets D1 and D2 which respectively contain the microparticles A1 and A2.

In the example shown in FIGS. 6A to 6C, even if the microparticles A1 and A2 are contained in the same droplet clock, the phase only changed by ($\phi 2-\phi 1$) (refer to FIG. 6B). Therefore, in a case in which the microparticles A1 and A2 are contained in different droplets D1 and D2, when the delay time is set to the provisional delay time, there are cases in which the timing of the charge application to the desired droplet deviates (refer to FIG. 6C). Therefore, in order to more accurately determine the timing when to apply the charge to the droplets, it is necessary to adjust the delay time to an interval (hereinafter referred to as the phase) shorter than the droplet clock.

FIGS. 7A to 7C show images that are imaged by the droplet camera 4 at different phases in relation to the same droplet clock. More specifically, FIGS. 7A to 7C show images of the microparticles that are imaged by the droplet camera 4 at each phase (FIG. 7A PHY=0, FIG. 7B PHY=90, FIG. 7C PHY=270) in relation to the same droplet clock. Among the phases where the time of the same droplet clock is divided into 360 phases, FIGS. 7A to 7C respectively show the images in relation to the 0th phase (FIG. 7A PHY=0), the 90th phase (FIG. 7B PHY=90), and the 270th phase (FIG. 7C PHY=270) in time series order.

As illustrated with reference to FIGS. 6A to 6C, since there are cases in which different droplets D1 and D2 contain the microparticles A1 and A2 within the same droplet clock, in the example shown in FIG. 7A, it is also possible to detect the bright spots B in the comparison region (Section 0) adjacent to the standard region (Section 1) using the control unit 7. In other words, the control unit 7 discriminates that there are microparticles within the comparison region (Section 0). In addition, in the example shown in FIG. 7C, bright spots B are also detected in the other comparison region (Section 2) adjacent to the standard region (Section 1). In other words, the control unit 7 discriminates that there are microparticles within the comparison region (Section 2).

In the present step $S_6$, this makes it possible for the control unit 7 to discriminate the phase deviation (the delay phase), to update the provisional delay time, and to determine the delay time. More specifically, the control unit 7 updates the provisional delay time and determines the delay time by referring to the adjacent information relating to the number of the bright spots B of one of the comparison regions of the two comparison regions that are adjacent to the standard region in relation to the discharge direction of the droplets D in the image information. Detailed description will be given below of the first delay time determination method and the second delay time determination method as specific determination methods of the delay time with reference to FIG. 8 to FIG. 11.

Furthermore, here, description is given of an example where the bright spots B are detected in two regions (the two regions of "Section 1" and "Section 0" or "Section 2"), however, even in a case in which the bright spots are detected in the three regions of "Section 1", "Section 0", and "Section 2", it is possible to determine the delay time in the same manner as in the first delay time determination method or the second delay time determination method described below.

2-6-1 First Delay Time Determination Method

Figure 8:
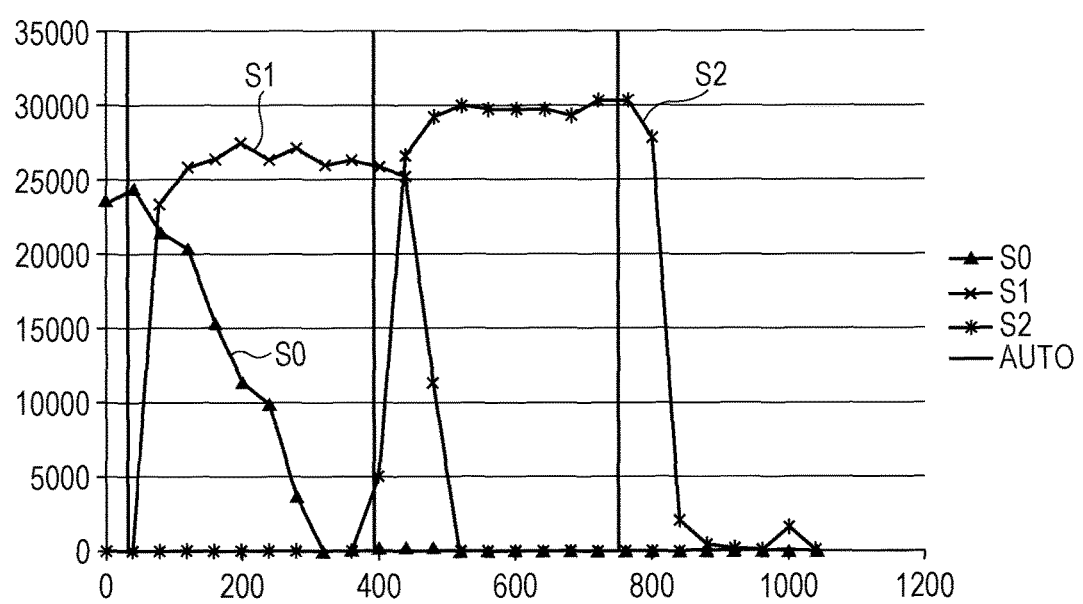
FIG. 8 is an explanatory diagram, which is a graph in which the horizontal axis is the phase, and the vertical axis is the number of bright spots of the images of the droplets imaged by the droplet camera of the flow cytometer, for illustrating an example of the delay time determination step (the first delay time determination method)
Figure 9:
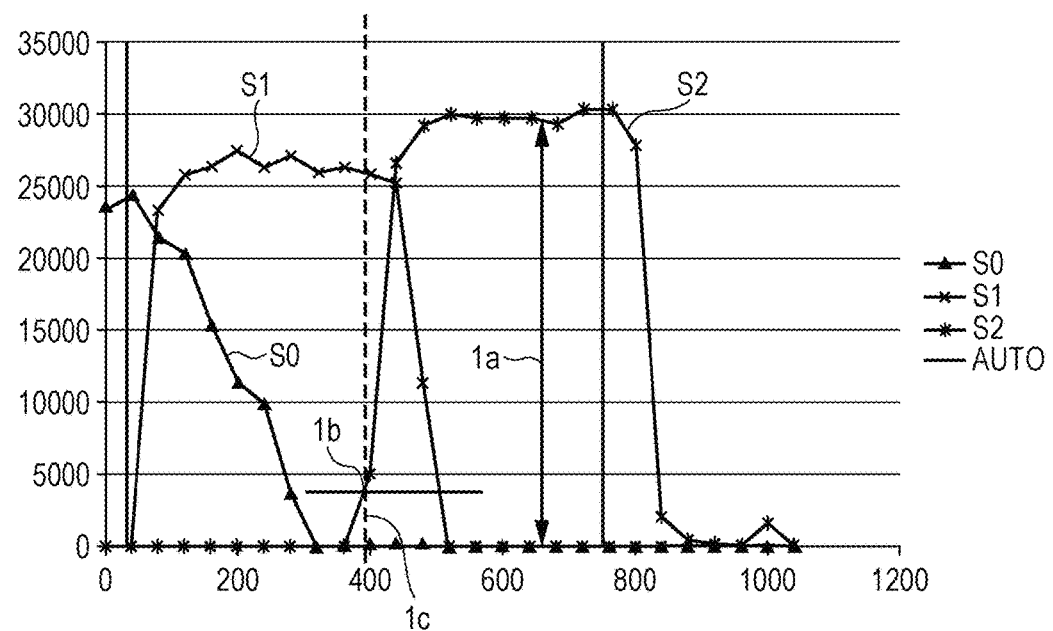
FIG. 9 is an explanatory diagram, which is a graph in which the horizontal axis is the phase, and the vertical axis is the number of bright spots of the images of the droplets imaged by the droplet camera of the flow cytometer, for illustrating an example of the delay time determination step (the first delay time determination method)

First, description will be given of the first delay time determination method with reference to FIG. 8 and FIG. 9, in which the delay time is determined by referring to the bright spots of only "Section 2 (S2)" of the two comparison regions. FIG. 8 and FIG. 9 are graphs in which the horizontal axis is the phase value, and the vertical axis is the number of bright spots of the image of the droplets imaged by the droplet camera 4 of the flow cytometer 1. More specifically, in the graphs, as shown in FIG. 8, the number of bright spots in the three regions of "Section 0 (S0)", "Section 1 (S1)", and "Section 2 (S2)" is shown.

First, in relation to "Section 1 (S1)", the control unit 7 calculates the maximum value of the number of bright spots in "Section 2 (S2)" of the two comparison regions, which is positioned at the positive direction side of the discharge direction of the droplets (refer to FIG. 9, (1a)).

Next, the control unit 7 calculates the time at which the number of bright spots reaches 10% of the maximum value described above in the process where the number of bright spots increases toward a maximum in "Section 2 (S2)" (refer to point (1b) and point (1c) in FIG. 9).

Finally, the control unit 7 sets the time at which the number of bright spots reaches 10% of the maximum value as time at which the maximum number of bright spots is reached within the standard region, and determines the delay time. In other words, the control unit 7 calculates the phase value in relation to the point (1b) and the point (1c) and determines the delay time based on the phase value.

According to the above, in the flow cytometer 1, the control unit 7 calculates the delay time by referring to the adjacent information relating to the number of the bright spots in the comparison region positioned in the positive direction side of the discharge direction of the droplets of the two comparison regions that are adjacent to the standard region in relation to the discharge direction of the droplet D in the image information. In this manner, in the flow cytometer 1, it is possible to accurately and automatically apply the charge to the droplets without concerns that phase shifting will occur between the synchronized droplets and the charge signal.

Furthermore, the first delay time determination method, which is an example of the present step $S_6$, is used favorably in a case in which the detection of the microparticles contained in the sample is performed in the microchip 2 and the application of charge to the droplet D is performed in air. In other words, the speed of the sample varies between inside the microchip 2 and in the air, and therefore in a case in which it is necessary to adjust the timing at which the charge is applied to the sample, it is particularly effective to determine the delay time using the first delay time determination method.

In addition, description is given of a case in which, in the first delay time determination method, the control unit 7 calculates the phase value based on the value at which the number of bright spots reaches 10% of the maximum in the comparison region, however, the present technology is not limited to this example. For example, it is also possible for the control unit 7 to determine an appropriate delay time by calculating X % (where X is, for example, an arbitrary value such as 5 or 20) of the maximum number of bright spots.

2-6-2 Second Delay Time Determination Method

Figure 10:
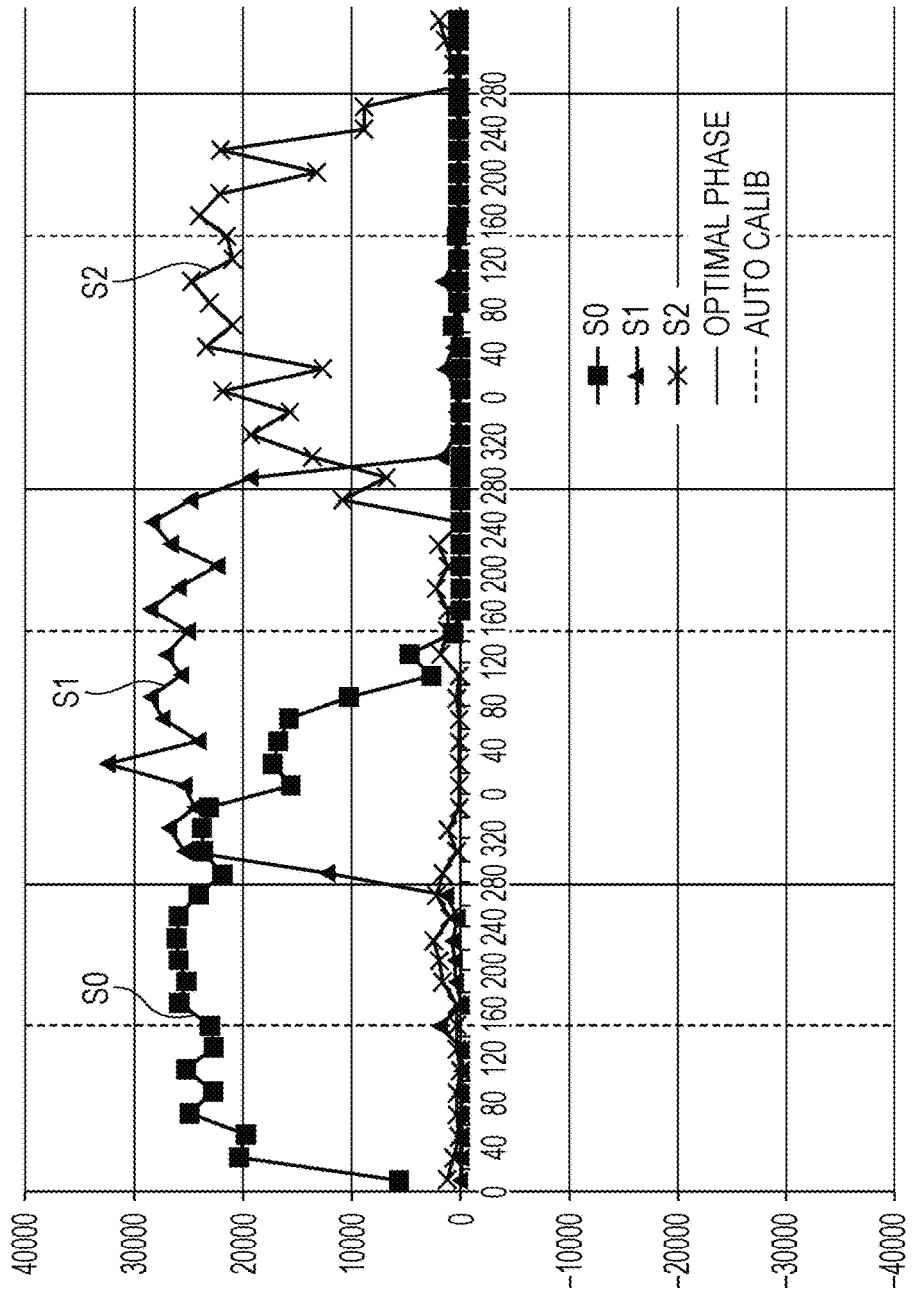
FIG. 10 is an explanatory diagram, which is a graph in which the horizontal axis is the phase, and the vertical axis is the number of bright spots of the images of the droplets imaged by the droplet camera of the flow cytometer, for illustrating an example of the delay time determination step (the second delay time determination method)
Figure 11:
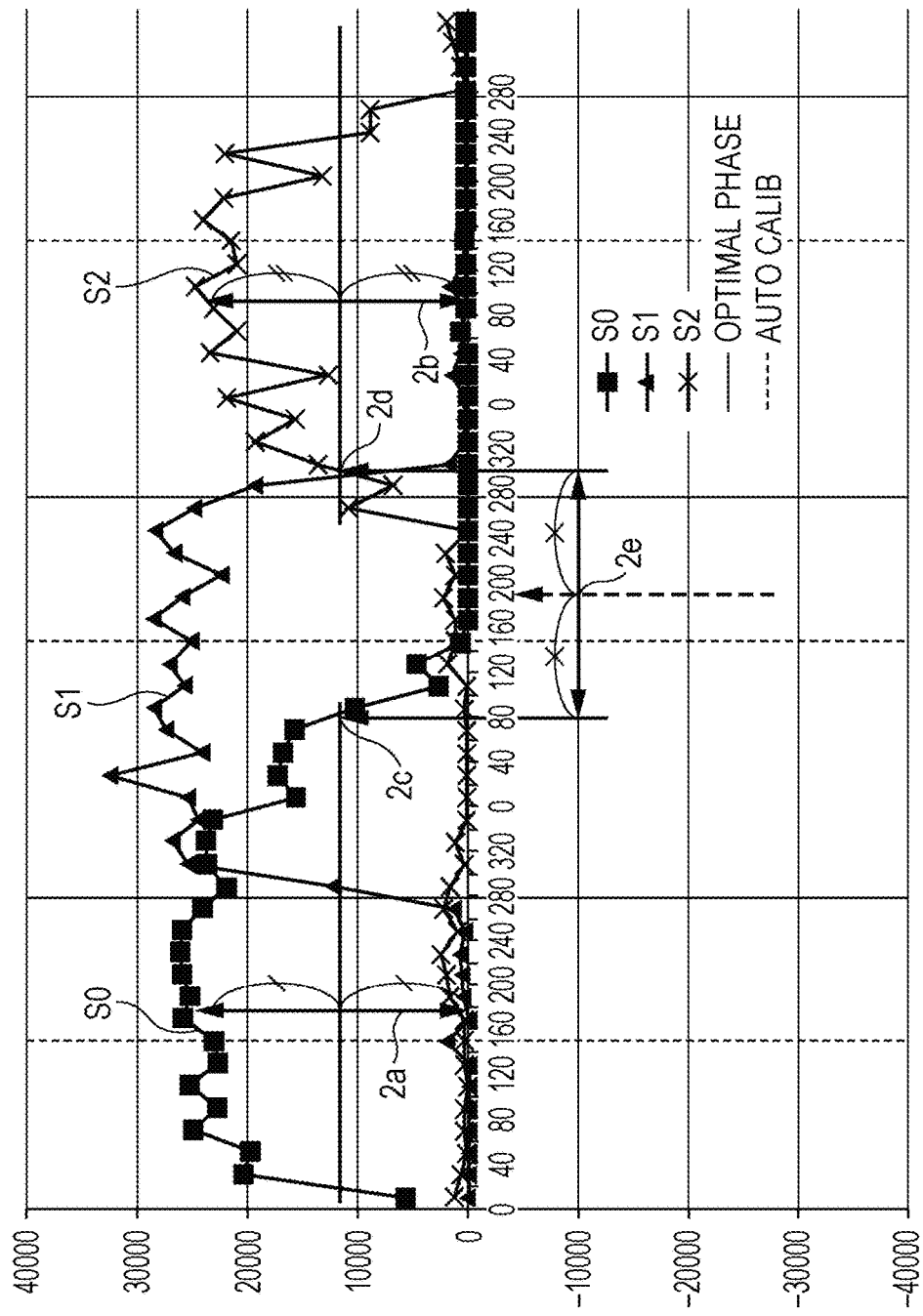
FIG. 11 is an explanatory diagram, which is a graph in which the horizontal axis is the phase, and the vertical axis is the number of bright spots of the images of the droplets imaged by the droplet camera of the flow cytometer, for illustrating an example of the delay time determination step (the second delay time determination method)

Next, description will be given of the second delay time determination method with reference to FIG. 10 and FIG. 11, in which the delay time is determined by referring to the bright spots of the two comparison regions Section 0 (S0) and Section 2 (S2). FIG. 10 and FIG. 11 are graphs in which the horizontal axis is the phase value, and the vertical axis is the number of bright spots of the image of the droplets imaged by the droplet camera 4 of the flow cytometer 1. More specifically, in the graphs, as shown in FIG. 10, the number of bright spots in the three regions of Section 0 (S0), Section 1 (S1), and Section 2 (S2) is shown.

First, in relation to Section 1 (S1), the control unit 7 calculates the average value of the maximum value and the minimum value of the number of bright spots in Section 0 (S0) of the two comparison regions, which is positioned at the negative direction side of the discharge direction of the droplets (refer to FIG. 11, (2a)). In other words, as shown in FIG. 11, when the minimum value is 0, the control unit 7 calculates the value of the maximum value of the number of bright spots in Section 0 (S0) multiplied by ½ (hereinafter referred to as the median value in Section 0).

Next, in the same manner as the case of Section 0 (S0), in relation to Section 1 (S1), the control unit 7 calculates the average value of the maximum value and the minimum value of the number of bright spots in Section 2 (S2) of the two comparison regions, which is positioned at the positive direction side of the discharge direction of the droplets (refer to FIG. 11, (2b)). In other words, as shown in FIG. 11, when the minimum value is 0, the control unit 7 calculates the value of the maximum value of the number of bright spots in Section 2 (S2) multiplied by ½ (hereinafter referred to as the median value in Section 2).

Next, the control unit 7 calculates a first time at which the ½ of the maximum number of bright spots is reached in the process of the number of bright spots decreasing from the maximum in Section 0 (S0). In other words, the control unit 7 takes the median value in the Section 0, calculates a parallel straight line on the horizontal axis of the graph, and calculates the phase value of the point at which the straight line crosses the point at which Section 0 (S0) is plotted (refer to point (2c) in FIG. 11).

Next, the control unit 7 calculates a second time at which the ½ of the maximum number of bright spots is reached in the process of the number of bright spots increasing toward the maximum in Section 2 (S2). In other words, in the same manner as in the case of Section 0 (S0), the control unit 7 takes the median value in the Section 0, calculates a parallel straight line on the horizontal axis of the graph, and calculates the phase value of the point at which the straight line crosses the point at which Section 0 (S0) is plotted (refer to point (2d) in FIG. 11).

Finally, based on the first time and the second time, the control unit 7 determines the delay time as (first time+second time)/2. In other words, the control unit 7 calculates the median point (refer to point (2e) in FIG. 11) of the phase value in relation to the point (2c) and the point (2d) and determines the delay time with the phase value of the median point set as the maximum number of bright spots within the standard region.

According to the above, in the flow cytometer 1, the control unit 7 calculates the delay time by referring to the adjacent information relating to the number of the bright spots in the two comparison regions that are adjacent to the standard region in relation to the discharge direction of the droplets in the image information. In this manner, in the flow cytometer 1, it is possible to accurately and automatically apply the charge to the droplets without concerns that phase shifting will occur between the synchronized droplets and the charge signal.

Furthermore, the second delay time determination method, which is an example of the present step $S_6$, is used favorably in a case in which the sample is in the air from the position at which the microparticles contained in the sample are detected until the position (the point at which the values of S0 and S2 are calculated) at which the application of a charge to the microparticles is performed.

In addition, description is given of a case in which, in the second delay time determination method, the control unit 7 calculates the phase value with the value at which the number of bright spots reaches ½ of the maximum in the comparison region as the median value, however, the present technology is not limited to this example. For example, it is also possible for the control unit 7 to determine the delay time by calculating the median value as 1/Y (where Y is, for example, an arbitrary value such as 2, 3, or 4) of the value of X % (where X is, for example, an arbitrary value such as 90 or 80) of the maximum number of bright spots in the comparison region.

2-7 Microparticle Sorting Step $S_7$

Figure 12:
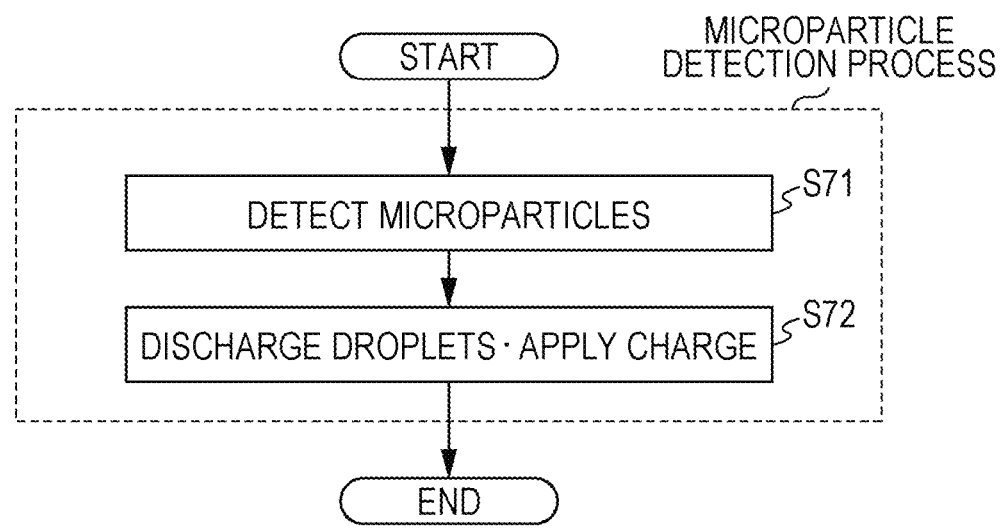
FIG. 12 is a flow diagram for illustrating the method of sorting the microparticles (the microparticle sorting step) in the flow cytometer.

FIG. 12 is flow chart for illustrating step $S_7$ in which microparticles such as cells are sorted in the flow cytometer 1. In the microparticle sorting step $S_7$, the flow cytometer 1 performs sorting of the droplets containing microparticles such as cells based on the delay time which is determined in steps $S_1$ to $S_6$ described above. A trajectory direction discrimination step includes the processes of "the microparticle detection step $S_{71}$" and "the droplet discharge and charge application step $S_{72}$". Description will be given of each process below.

2-7-1 Microparticle Detection Step $S_{71}$

First, in the present step $S_{71}$, the detection unit 3 detects the microparticles. The detection method may be performed in the same manner as the process in step $S_1$ described above.

2-7-2 Droplet Discharge and Charge Application Step $S_{72}$

Next, in the present step $S_{72}$, once the determined delay time has elapsed from the time at which the microparticles such as cells are detected by the detection unit 3, the control unit 7 outputs a signal to the charge unit 11 for performing charge application on the droplets containing the microparticles (refer to FIG. 12). Furthermore, the charge unit 11 applies a charge to the droplets.

In this manner, in the flow cytometer 1, it is possible to accurately and automatically apply a charge to the desired microparticles such as cells. In addition, in the flow cytometer 1, it is possible to apply a charge in a state in which the delay time has been determined. Therefore, by irradiating the droplet D using the laser L2 only once the provisional delay time has elapsed after the microparticles such as cells are detected by the detection unit 3, it is possible to accurately confirm that the droplet D contains the microparticles while reducing the usage amount of the laser.

The microparticle sorting apparatus and the delay time determination method according to the present technology may also adopt the following configurations.

(1) A microparticle sorting apparatus including a detection unit which detects microparticles flowing through a flow path; an imaging device which images droplets containing the microparticles which are discharged from an orifice provided on an edge portion of the flow path; a charge unit which applies a charge to the droplets; and a control unit which determines a delay time as from a time that the microparticles are detected by the detection unit to the time at which the number of bright spots in a standard region, which is set beforehand, of image information imaged by the imaging device reaches the maximum, making it possible for the charge unit to apply a charge to the microparticles once the delay time has lapsed after the microparticles are detected by the detection unit.

(2) The microparticle sorting apparatus according to (1), in which the imaging device images of a plurality of the droplets at a plurality of different times, and in which the control unit preliminarily determines the delay time using the time from when the microparticles are detected by the detection unit to the time at which the number of bright spots within the standard region, which is calculated by comparing the image information of the plurality of droplets imaged by the imaging device, reaches a maximum as a provisional delay time.

(3) The microparticle sorting apparatus according to (2), in which the imaging device images the images of the plurality of droplets within a shorter time than a discharge interval time of each of the droplets once the provisional delay time has elapsed from the time at which the microparticles are detected by the detection unit, and in which the control unit updates the provisional delay time and determines the delay time by referring to adjacent information relating to the number of the bright spots in at least one of two comparison regions that are adjacent to the standard region in relation to a discharge direction of the droplets in the image information.

(4) The microparticle sorting apparatus according to (3), in which, of the two comparison regions, a first comparison region and a second comparison region are arranged in order in a discharge direction of the droplets, and in which the control unit calculates the time at which the number of bright spots reaches a predetermined percentage of the maximum value in the second comparison region in a process where the number of bright spots increases toward the time at which the number of bright spots reaches the maximum in the second comparison region, and determines the time to be the time at which the number of bright spots within the standard region reaches the maximum.

(5) The microparticle sorting apparatus according to (3) or (4), in which, of the two comparison regions, a first comparison region and a second comparison region are arranged in order in a discharge direction of the droplets, in which the control unit calculates the first time at which the number of bright spots reaches a predetermined percentage of the maximum value in the first comparison region in a process where the number of bright spots decreases from the time at which the number of bright spots reaches the maximum in the first comparison region, calculates the second time at which the number of bright spots reaches a predetermined percentage of the maximum value in the second comparison region in a process where the number of bright spots increases toward the time at which the number of bright spots reaches the maximum in the second comparison region, and determines the time in which the number of bright spots within the standard region reaches the maximum as (the first time+the second time)/2.

(6) The microparticle sorting apparatus according to any one of (1) to (5), in which the control unit adjusts a discharge frequency of the droplets, and determines the optimal discharge frequency of the droplets to be the discharge frequency at which the break-off point, where the droplets start forming in the discharge direction of the droplets, is closest to the orifice.

(7) The microparticle sorting apparatus according to any one of (1) to (6), further including a pair of deflection plates disposed opposite one another to interpose the droplets imaged by the imaging device, which change a progression direction of the droplets using an electrical force which acts between the deflection plates and the charge.

(8) The microparticle sorting apparatus according to any one of (1) to (7), in which the microparticle sorting apparatus is a microchip-type flow cytometer in which the orifice and the flow path are provided in the microchip.

(9) A delay time determination method in a microparticle sorting device including causing a microparticle sorting device to detect microparticles flowing through a flow path; causing a microparticle sorting device to image a droplet containing the microparticles which is discharged from an orifice provided on an edge portion of the flow path; and causing a microparticle sorting device to determine a delay time as from a time that the microparticles are detected until the time at which a number of bright spots in a standard region, which is set beforehand, of image information of droplets that are imaged reaches the maximum.

(10) The delay time determination method according to (9), further including imaging the images of a plurality of the droplets at a plurality of times; and preliminarily determining the delay time using the period of from the time at which the microparticles are detected until the time at which the number of bright spots within the standard region, which is calculated by comparing the image information of the plurality of droplets which are imaged, reaches the maximum as the provisional delay time.

(11) The delay time determination method according to (10), further including imaging the images of the plurality of droplets within a shorter time than a discharge interval time of each of the droplets once the provisional delay time has elapsed from the time at which the microparticles are detected; and updating the provisional delay time and determining the delay time by referring to adjacent information relating to the number of the bright spots in at least one of two comparison regions that are adjacent to the standard region in relation to a discharge direction of the droplets in the image information.

(12) The delay time determination method according to (10), in which, of the two comparison regions, a first comparison region and a second comparison region are arranged in order in a discharge direction of the droplets, the method further including calculating the time at which the number of bright spots reaches a predetermined percentage of the maximum value in the second comparison region in a process where the number of bright spots increases toward the time at which the number of bright spots reaches the maximum in the second comparison region; and determining the time to be the time at which the number of bright spots within the standard region reaches the maximum.

(13) The delay time determination method according to (11) or (12), in which of the two comparison regions, a first comparison region and a second comparison region are arranged in order in a discharge direction of the droplets, the method further including calculating the first time at which the number of bright spots reaches a predetermined percentage of the maximum value in the first comparison region in a process where the number of bright spots decreases from the time at which the number of bright spots reaches the maximum in the first comparison region; calculating the second time at which the number of bright spots reaches a predetermined percentage of the maximum value in the second comparison region in a process where the number of bright spots increases toward the time at which the number of bright spots reaches the maximum in the second comparison region; and determining the time in which the number of bright spots within the standard region reaches a maximum as (the first time+the second time)/2.

The present disclosure contains subject matter related to that disclosed in Japanese Priority Patent Application JP 2012-080192 filed in the Japan Patent Office on Mar. 30, 2012, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A delay time determination method comprising:
   detecting, using a microparticle sorting device, microparticles flowing through a flow path;
   obtaining, using the microparticle sorting device, a plurality of images of a droplet including at least one of the microparticles, the plurality of images having a standard region in respective images of the plurality of images, and wherein the droplet is discharged from an orifice provided on an edge portion of the flow path; and
   determining a delay time by examining the standard region in respective images of the plurality of images and identifying an image of the plurality of images that has a maximum brightness characteristic within the standard region; and
   setting a timing for applying charge to droplets based on the delay time.

2. The delay time determination method according to claim 1,
   wherein determining the delay time further comprises comparing a brightness characteristic in at least one comparison region to a brightness characteristic in the standard region for an image of the plurality of images, wherein the at least one comparison region is adjacent to the standard region along a discharge direction of the droplets in the image.

3. The delay time determination method according to claim 2, wherein the at least one comparison region includes a first comparison region and a second comparison region arranged on opposite sides of the standard region, and
   determining the delay time further comprises determining the delay time based on a brightness characteristic in the first comparison region and a brightness characteristic in the second comparison region.

4. The delay time determination method according to claim 3, the method further comprising:
   calculating a first time at which a brightness characteristic of the first comparison region reaches a predetermined percentage of a maximum value;
   calculating a second time at which a brightness characteristic of the second region reaches a predetermined percentage of the maximum value; and
   determining a time for the standard region as (the first time+the second time)/2.

5. The delay time determination method according to claim 3, the method further comprising:
   adjusting a discharge frequency of the droplets based on the delay time; and
   determining an optimal discharge frequency of the droplets to be the discharge frequency at which a point where the droplets are formed is proximate to the orifice.

6. The delay time determination method according to claim 1, wherein obtaining the plurality of images further comprises obtaining the plurality of images based on a time when one of the microparticles is detected by the microparticle sorting device.

* * * * *